United States Patent [19]
Newton

[11] 3,963,030
[45] June 15, 1976

[54] SIGNAL GENERATING DEVICE AND METHOD FOR PRODUCING COAGULATION ELECTROSURGICAL CURRENT

[75] Inventor: David W. Newton, Boulder, Colo.

[73] Assignee: Valleylab, Inc., Boulder, Colo.

[22] Filed: Nov. 1, 1974

[21] Appl. No.: 520,219

Related U.S. Application Data

[63] Continuation of Ser. No. 351,232, April 16, 1973, abandoned.

[52] U.S. Cl. .............................. 128/303.17; 323/4; 323/17
[51] Int. Cl.² ......................................... A61B 17/36
[58] Field of Search ................ 128/303.14, 303.17; 321/4; 323/1, 4, 16, 17, 19, 22 T, DIG. 1

[56] References Cited
UNITED STATES PATENTS

| | | | |
|---|---|---|---|
| 3,436,563 | 4/1969 | Regitz | 323/4 UX |
| 3,471,770 | 10/1969 | Haire | 323/1 |
| 3,562,623 | 2/1971 | Farnsworth | 323/DIG. 1 |
| 3,601,126 | 8/1971 | Estes | 128/303.14 |
| 3,641,422 | 2/1972 | Farnsworth et al. | 323/DIG. 1 |
| 3,699,967 | 10/1972 | Anderson | 128/303.14 |

Primary Examiner—A. D. Pellinen
Attorney, Agent, or Firm—Gerald J. Ferguson, Jr.; Joseph J. Baker

[57] ABSTRACT

A signal generating device and method for producing an RF output signal regulated in power and of decaying amplitude suitable for use in an electrosurgical generator for surgical coagulation purposes. The device includes a circuit tuned to a predetermined radio frequency suitable to prevent nerve stimulation and the tuned circuit has connected therewith an unregulated power supply with current through the tuned circuit being controlled by means of a solid state switching system. The tuned circuit includes an inductor initially charged to a predetermined energy level. The switching system is automatically controlled so that the switching system is repeatedly urged to the closed position at predetermined time intervals and remains in this position until the current through the tuned circuit reaches a predetermined level at which time the switching system is caused to open and the tuned circuit thereafter rings to produce a regulated output signal of decaying amplitude, this output being taken from the tuned circuit across a transformer and is well suited for surgical coagulation purposes wherein the electrical current passes from an electrode to body tissue in the form of an arc with power dissipation being far greater in the tissue than in the arc for best operation.

3 Claims, 6 Drawing Figures

SIGNAL GENERATING DEVICE AND METHOD FOR PRODUCING COAGULATION ELECTROSURGICAL CURRENT

CROSS REFERENCE TO RELATED APPLICATIONS 11

This application is a continuation of U.S. patent application Ser. No. 351,232 filed Apr. 16, 1973 by David W. Newton, now abandoned.

BACKGROUND OF THE INVENTION

1. Field of the Invention

This invention relates to an electrosurgical apparatus and method and more particularly relates to signal generation suitable for use in producing electrosurgical coagulation currents.

2. Description of the Prior Art

Heretofore, varying types of electrosurgical generators have been proposed and/or utilized that have been capable of generating cutting and/or coagulation currents. As is well known, such an electrosurgical generator supplies electrical power to be used for localize heating of tissues in surgical cutting and surgical coagulating. Such a generator is shown, for example, in U.S. Pat. No. 3,699,967, issued Oct. 24, 1972. In order to prevent nerve stimulation, the power supply to the tissues must be supplied at radio frequencies, and for surgical coagulation, electrical current passes from an electrode to the body tissue in the form of an arc. In order to generate such an arc, the electrosurgical generator must have a high voltage capability both to start and sustain such an arc. While electrosurgical generators suitable for producing surgical coagulation currents have been proposed and used heretofore, none of these electrosurgical generators have been found to be completely successful for at least some purposes, and it has been found that at least some such generators have requied expensive and complicated circuitry, have been limited in performance capabilities, and/or have not been as efficient in operation as thought desirable.

SUMMARY OF THE INVENTION

This invention provides a signal generating device and method that is well suited for producing coagulation electrosurgical currents. The signal generating device includes a circuit that is tuned to a predetermined frequency with the tuned circuit being connectable with a power source and switching means that controls current flow from the power source to the tuned circuit. The switching means is controlled so that current is permitted to flow to the tuned circuit during a first predetermined time period and prevented during a second predetermined time period with the tuned circuit being permitted to ring during the second predetermined time period so that the output taken from the tuned circuit is a decaying RF output signal. The current through the tuned circuit is sensed and the power thereto disrupted when a predetermined level is reached so that the RF decaying output signal from the circuit is a regulated output.

It is therefore an object of this invention to provide an improved signal generating device and method for producing signals. It is another object of this invention to provide an improved signal generating device for producing coagulation electrosurgical currents, as well as an improved method for producing such signals.

It is still another object of this invention to provide an improved signal generating device that is relatively simple yet provides good performance capabilities and is efficient in operation.

It is still another object of this invention to provide an improved signal generating device that does not require expensive and complicated circuitry in order to provide a regulated RF decaying output signal that is well suited for producing electrical coagulation currents.

It is still another object of this invention to provide an improved signal generating device for use as part of an electrosurgical generator that may be utilized with an unregulated power supply to produce a regulated (i.e., the power of the output signal does not change as a function of the line input voltage) RF output signal of decaying amplitude that is well suited for surgical coagulation purposes.

It is still another object of this invention to provide in an electrosurgical generator a tuned circuit including an inductor initially charged to a predetermined energy level.

With these and other objects in view, which will become apparent to one skilled in the art as the description proceeds this invention resides in the novel construction, combination, and arrangement of parts substantially as hereinafter described and more particularly defined by the appended claims, it being understood that such changes in the precise embodiment of the herein disclosed invention are meant to be included as within the scope of the claims.

BRIEF DESCRIPTION OF THE DRAWINGS

The accompanying drawings illustrate one complete embodiment of the invention according to the best mode so far devisd for the practical application of the principles thereof, and in which.

DESCRIPTION OF THE PREFERRED EMBODIMENT

Figure 1:
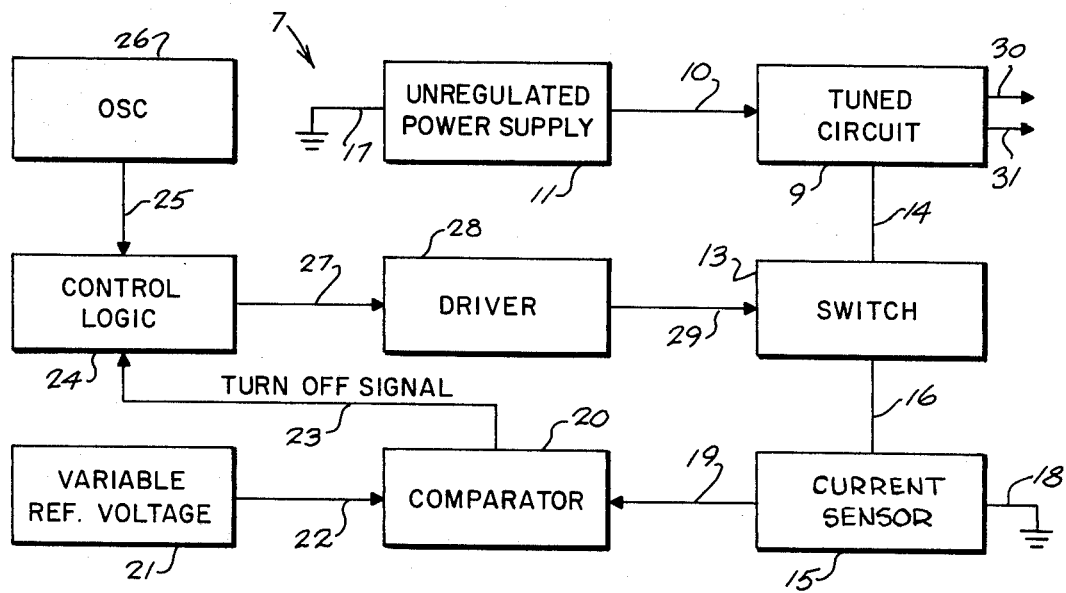
FIG. 1 is a block diagram illustrating the signal generating device of this invention.

Referring now to the drawings in which like numerals have been used for like characters throughout, the numeral 7 indicates generally the signal generating device of this invention, which device includes a tuned circuit 9 having connected thereto by means of lead 10 an unregulated power supply 11. The current flow to the tuned circuit from the power supply is controlled by switch 13 one side of which is connected to tuned circuit 9 through lead 14 and the other side of which is connected with a current sensor 15 through lead 16. To complete the circuit, power supply 11 and current sensor 15 are returned to ground through leads 17 and 18, respectively. The output from current sensor 15 is coupled through lead 19 to comparator 20 which has a variable reference voltage 21 also coupled thereto by lead 22, with the output from the comparator being a turnoff signal that is coupled by lead 23 to control logic 24. Control logic 24 has also coupled thereto by lead 25 the output from conventional oscillator 26 with the output from the control logic being coupled by leads 27 to driver 28, the output of which is coupled by lead 29 to switch 13. The output from the circuit is a regulated RF output of decaying amplitude and is coupled from the circuit by means of leads 30 and 31.

It has been found that four criteria must be successfully met for best results to be achieved in a surgical electro-coagulator. These criteria are: the open circuit potential must be high (about 8 to 10 kilovolts peak-to-peak); power content must be in the high frequency range (about 300 kHz and higher); a satisfactory crest factor must be attained (between about 5 to 10); and sufficient total output power must be achieved (50–100 watts maximum). The crest factor is determined by the relationship $[I_{op}/n] [R_1/P_o]$ where $I_{op}$ is the current through inductor (transformer primary 34) L when the switch opens, n is the turns ratio of the transformer 35, $R_1$ is the load and $P_o$ is the output power.

In a surgical coagulation device of the type shown in FIG. 1, power is dissipated both in the arc itself and the immediately surrounding tissue. The balance between the two dissipations depends upon the relative impedances between the two. The arc will normally display a non-linear impedance characteristic so that the higher the instantaneous current the lower will be the instantaneous impedance. On the other hand, body tissue offers a relatively linear impedance with increases in current so that if the electrosurgical output consists of short high power pulses, as is preferable, a large part of the power will be dissipated in the tissue and only a small part in the arc. The property of the wave form governing this effect is the crest factor which is defined as the peak value in voltage or current divided by the rms value. It has been found that a crest factor of about 5 to 10 gives a good balance between the two dissipations.

Figure 2:
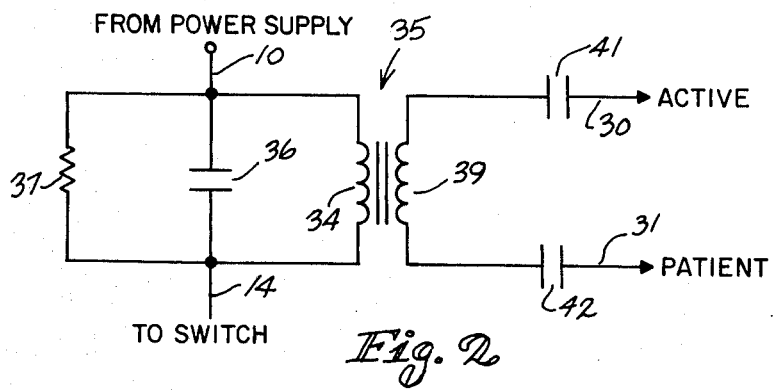
FIG. 2 is an electrical schematic diagram illustrating the type of tuned circuit that may be utilized as the tuned circuit shown in block form in FIG. 1.

With respect to FIG. 1, it can be seen that when the switch 13 is closed current will flow through the tuned circuit, and if the tuned circuit is a parallel RLC circuit, as indicated in FIG. 2, current flow will be through the inductor in the tuned circuit. This current through the inductor will increase linearly if $di/dt=V/L_p$ where V is the circuit voltage and $L_p$ is the transformer primary inductance (assuming the V/R is small) after the time that C is charged to V. When switch 13 is then opened, the tuned circuit will thereafter ring and the voltage will fluctuate according to the well known operation of an RLC circuit, as indicated by the typical wave form of FIG. 5.

The energy stored in the inductor dissipates in the resistance 37 and the load which is connected to the tuned circuit. The portion dissipated in the load depends upon the relation which the primary-reflected equivalent of the impedance of the load bears to the resistance by the well known rules of parallel impedance. For reasonable values of load impedance between 2K and 200 ohms, at least ten times more power is dissipated in the load impedance than in the resistance.

Figure 5:
FIG. 5 is a typical wave form present at the tuned circuit of this invention during normal operation.
Figure 3:
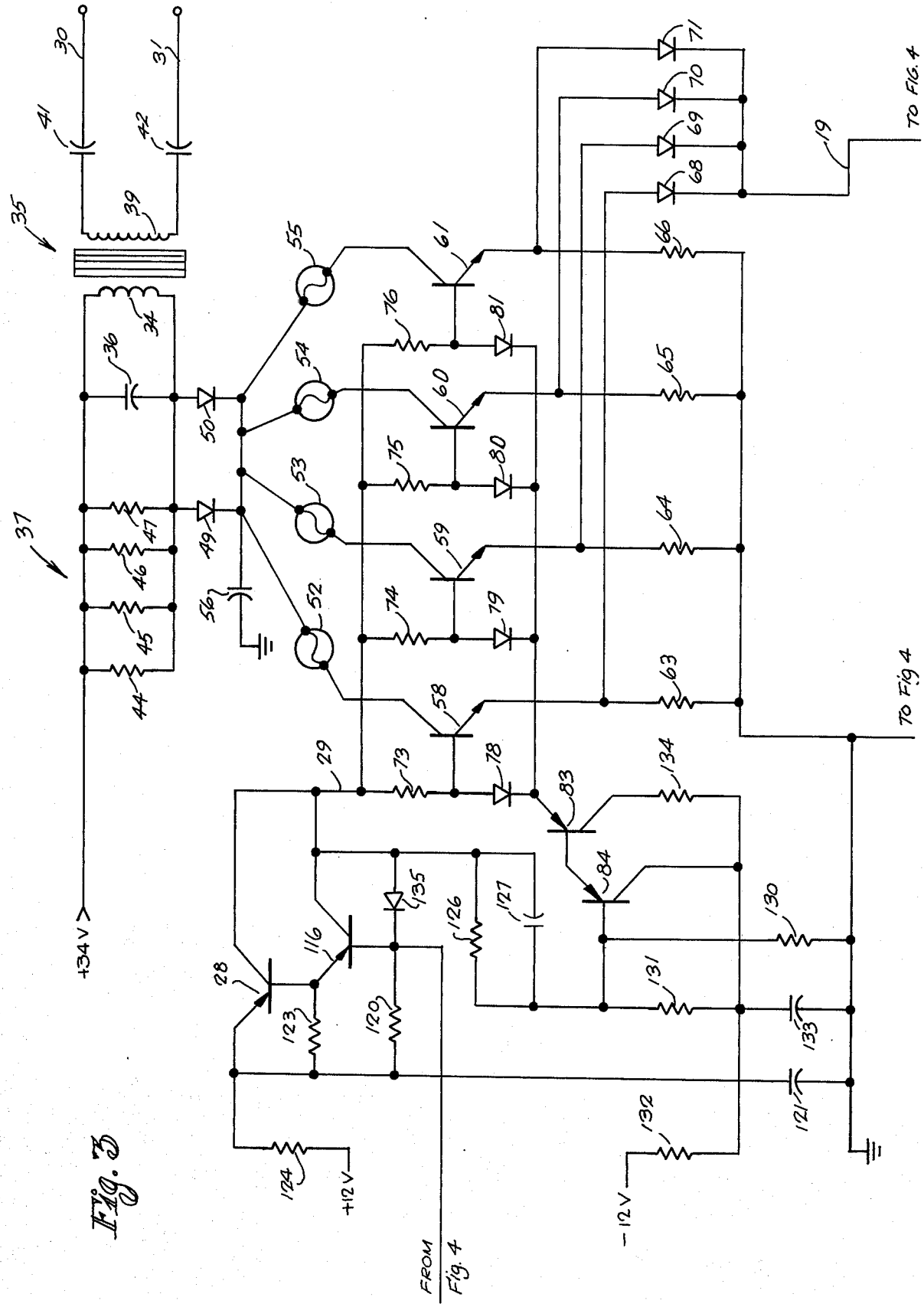
FIG. 3 is an electrical schematic diagram illustrating the tuned circuit, switch, current sensor, and driver shown in block form in FIG. 1.

To provide the necessary output for surgical coagulation the tuned circuit is driven repeatedly by means of oscillator 26 so that the output appears as damped pulses of RF energy evenly spaced in time as indicated in FIG. 5. As shown in FIGS. 1, 2 and 3, the output is taken from the tuned circuit by leads 30 and 31.

The signal generating device of this invention has an output regulated so that the power is independent of the voltage source so that an unregulated power source can be utilized and still a regulated output achieved. When the current sensed by current sensor 15 and coupled to comparator 20 is sufficiently high to exceed that of variable reference voltage 21 (which is also coupled to comparator 20), then comparator 20 produces an output which is coupled to the logic circuitry 24 and causes switch 13 to assume the open position to disrupt the power supply to the tuned circuit. Thus, a regulated output is achieved even though the power supply is an unregulated voltage source. By providing a tuned circuit having a resonant frequency much greater than 60 Hz, the regulation process also compensates for line frequency ripple so that the voltage source need only be a simple rectified supply with only nominal filtering.

To satisfy the four criteria above set forth, it has been found that the tuned circuit should have the inductance and capacitance chosen so that the free ringing frequency of the RLC circuit is between 300 and 400 kHz, the circuit frequency, current, inductor and damping factor chosen so that the crest factor is 6 with a typical load impedance of 800 ohms, the turns ratio of the transformer 35 chosen so that the output potential is 9 KV peak to peak within the constraints of the peak voltage of the tuned circuit, and output power capability chosen to be about 60 watts maximum.

It has also been found preferable that the frequency of operation be chosen to be ultrasonic to thus make an essentially noiseless output. In addition, by use of semiconductor components that can be easily controlled with respect to conductivity, the conduction period can be readily varied as desired, and since a roughly constant amount of energy is stored in the inductor (transformer primary) of the tuned circuit for a given current flow, the output power is roughly independent of the load impedance.

Turning now to FIG. 2, a simplified parallel RLC circuit is illustrated. As shown, tuned circuit 9 includes the primary winding 34 of transformer 35 and has connected in parallel therewith the capacitor 36, both of which are connected in parallel with resistor 37 to form a parallel RLC circuit. The output from the tuned circuit is taken from the secondary winding 39 of transformer 35 through capacitors 41 and 42 and leads 30 and 31. As is well known in the art, such outputs are coupled to an active electrode and patient as shown, for example, in U.S. Pat. No. 3,699,967.

Figure 6:
FIG. 6 is a typical wave form present at the switching means of this invention during normal operation.

The preferred embodiment of tuned circuit 9 is shown in FIG. 3 wherein resistor 37 consists of four parallel connected resistors 44, 45, 46 and 47, and the secondary to primary of transformer 35 has a turns ratio of 9 to 1. As shown in FIG. 3, the tuned circuit is connected at one side to a +34 volt unregulated power source, which source has not been set forth in detail herein since it is to be understood that such source can be a conventional unregulated high current supply. Tuned circuit 9 is likewise connected by a pair of diodes 49 and 50 to four parallel connected fuses 52, 53, 54 and 55, the junction between the diodes and the fuses being connected with ground by bypass filter 56. The four fuses are directly connected to the collectors of transistors 58, 59, 60 and 61, which transistors serve as switching means 13 as indicated in the block diagram of FIG. 1. The rectified output present at transistors 58, 59, 60 and 61 is shown in FIG. 6 of the drawings.

Figure 4:
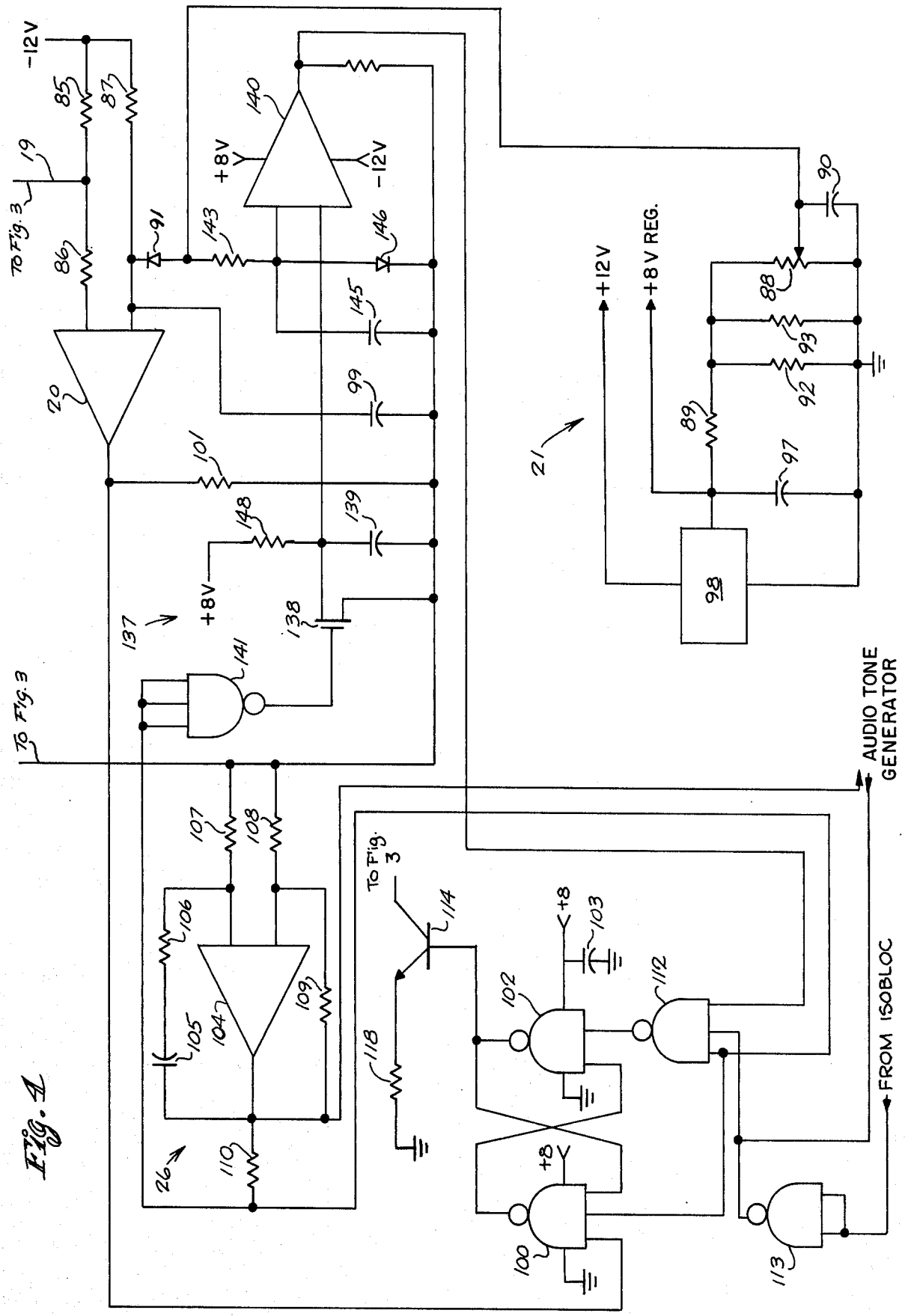
FIG. 4 is an electrical schematic diagram illustrating the comparator, variable reference voltage, control logic, and oscillator shown in block form in FIG. 1.

As shown in FIGS. 3 and 4, the emitters of each of the transistors 58–61 return to ground through resistors 63, 64, 65 and 66, which resistors serve as current sensors and are connected with comparator 20 through diodes 68, 69, 70 and 71 connected in common with lead 19. In addition, the bases of transistors 58–61 are connected through resistors 73, 74, 75 and 76 and common lead 29 to driver 28. Also, the bases of transistors 58–61 are connected through diodes 78, 79, 80 and 81 to the emitter of transistor 83, which acts in conjunction with transistor 84 to speed turnoff of transistors 58–61 for better operation.

A −12 volt source of power (not shown) is connected through resistor 85 to junction of resistor 86 and lead 19. In addition, the −12 volt source of power is connected through resistor 87 to a second input to the comparator, which also receives on this input an input from the variable reference voltage 21, which, as shown in FIG. 4, is coupled through diode 91 from a variable potentiometer 88 which is connected through resistor 89 to a +8 volt regulated power source (not shown). Potentiometer 88 has a bypass capacitor 90 to ground connected therewith. In addition, potentiometer 88 has parallel connected resistors 92 and 93 connected therewith as well as parallel connected capacitor 97 connected at one side thereof through resistor 89, the junction of capacitor 97 and resistor 89 being connected to the +8 volt regulated source of power (not shown). An integrated chip circuit 98 connected as shown as a voltage regulator is connected to the junction of resistor 89 and capacitor 97, this circuit also being connected as shown in FIG. 4, to the +12 volt power source (not shown) and to ground.

The output from comparator 20 (shown as an operational amplifier in FIG. 4) is connected through NAND gate 100 to NAND gate 102 which serves in conjunction with oscillator 26 as a flip-flop circuit. In addition, a grounded resistor 101 is connected with the output of comparator 20 while a by-pass capacitor 99 to ground is connected with one input. This output resets the flip-flop circuit to switch 13 (i.e., cease conduction of transistors 58–61) when the sensed current level is at the predetermined level exceeding that of the variable voltage source, as shown in FIG. 4, NAND gates 100 and 102 are connected to the +8 volt power source (not shown) and gate 102 has a by-pass capacitor 103 to ground.

Oscillator 26 includes an operational amplifier 104 having connected therewith series connected capacitor 105 and resistor 106, grounded resistors 107 and 108, and resistor 109. The output from the oscillator is taken through resistor 110 to NAND gate 112 the output of which is coupled to NAND gate 102 as the set signal (the normal reset being coupled through NAND gate 100 from comparator 20).

An input to logic control 24 through isolating circuitry (such as shown, for example, in U.S. Pat. No. 3,699,967 or U.S. application Ser. No. 318,177, now U.S. Pat. No. 3,801,800, filed Dec. 26, 1972 by David W. Newton and entitled "Isolating Switching Circuit for An Electrosurgical Generator") may also be provided. Such an input, as indicated in FIG. 4, may be provided through NAND gate 113, the output of which is coupled to NAND gate 112. In addition, oscillator 26 and control logic 24 may also be connected with a conventional audio tone generator, if desired, as indicated in FIG. 4.

In operation, the output from oscillator 26 sets NAND gate 102 at the leading edge of each oscillation to cause transistors 58–61 to assume their conductive states and thereafter apply current through the tuned circuit. Thus, the frequency of oscillator 26 determines the repetition rate of the decaying output signal produced by the signal generating device which decaying output signal has a frequency determined by the resonant frequency of the tuned circuit. It has been found that an oscillator operating at 21 kHz is satisfactory for a tuned circuit that is tuned to 400 kHz. The output from the control logic 24 (which includes the NAND gate) is coupled through transistor 114 to the base of transistor 116 in the driver stage. The emitter of transistor 114 is connected to ground through resistor 118 and the emitter of transistor 116 is connected to the base of driver transistor 28. As shown in FIG. 3, the base of transistor 116 is connected by means of resistor 120 and bypass capacitor 121 to ground, and the emitter of transistor 116 is connected through resistor 123 and bypass capacitor 121 to ground, while the emitter of transistor driver 28 is connected to bypass capacitor 121 to ground. In addition, the junction of the emitter of transistor 28 and resistors 120 and 123 is connected with the +12 volt power source (not shown) through resistor 124. The collector of transistor 28 is connected to the collector of transistor 116 and to the base of transistors 58–61 through lead 29 and resistors 73–76 as brought out hereinabove. Resistor 126 and capacitor 127 are connected as a parallel RC circuit between the collector of transistors 28 and 116 and transistor 84, the junction of which is connected with ground through resistor 130 and to the 12 voltage source through resistors 131 and 132. A bypass capacitor 133 to ground is connected to the junction of resistor 131 and 132. In addition, the collector of transistor 83 is collected to the −12 volt power supply through resistors 134 and 132, while the base and collector of transistor 116 has a diode 135 therebetween.

To preclude an erroneous signal at turn-on, an extended set pulse is provided by a monostable multivibrator 137 that is formed by transistor 138, capacitor 139, operational amplifier 140 and NAND gate 141. The width of this pulse is controlled by the controlled voltage from variable regulated voltage source 21 coupled to operational amplifier 140 through resistor 143 as shown in FIG. 4. Amplifier 140 has parallel connected capacitor 145 and diode 146 connected therewith, while transistor 138 is connected to the +8 volt power source (not shown) through resistor 148.

In operation, when solid state switch 13 is closed (i.e., transistors 58–61 in a conductive state), current flows through the tuned circuit and more particularly through the primary winding of transformer 35 causing a voltage across the inductor (the to primary). This voltage causes the the current through the inductor to increase linearly. When the switch is open (transistors 58–61 cease to conduct), as will be the case when the voltage sensed by resistors 63–66 reaches the level so that it is equal to or exceeding that of the variable reference voltage from source 21, comparator 20 will produce a reset pulse which will cause the logic 24 to reset the flip-flop and cause transistors 58–61 to cease conduction. The opening of switch 13 (by causing transistors 58–61 to be in a non-conductive state) will then cause the current in the inductor to ring with the parallel capacitor 36, the ringing being damped by the load and resistors 44–47 (as shown in FIG. 3) connected in parallel in the RLC circuit to thus provide a damped sinusoidal output.

The output power $P_o$ is roughly equal to $\frac{1}{2} L_p I_{op}^2 fN$ where $L_p$ is the inductance of the primary of the transformer, $I_{op}$ is the current through L when the switch opens, f is the repetition rate at which the switch is opened and closed, and N is efficiency at which the power is transferred to the load, N being dependent upon the load according to the relation that its primary reflected impedance bears to the effective resistance. The effective resistance of the circuit shown in FIG. 3 is preferably 750 ohms. When the load is equal to $R_1 = 750 \times n^2 = 60.75K$ ohms, about half the output will be dissipated in the load, and for larger impedances, less will be dissipated in the load. For low values of load impedance, the reflection of the load in the primary is such that little current flows through the primary. For this reason, the output decreases at low load impedances.

The current in the tuned circuit and thus the output power is regulated by the following process:

The oscillator 26 and NAND gate 102 form a type of flip-flop which is open on each leading edge of the oscillator 26. A reset signal comes from the comparator which derives its output from the highest of the voltages across sensing resistances 63–66. This voltage is directly related to the current in the tuned circuit in the following relation $V_{R63} = (I_o/4 + I_b) R_{63}$ where $I_b$ is the base current of the transistor 58. This voltage is compared with the well controlled regulated voltage ($V_c$) of the variable reference voltage which is set by the control potentiometer 88. When this voltage exceeds that of the variable reference voltage, then the flip-flop is reset, $I_{op}(V_c)$ then is $I_{op} = 4(V_c/R_{63} - I_b)$, the subtracted term $I_b$ is related to the value of the +12 volt unregulated power supply. Thus, changes in the unregulated +12 volt power supply causes changes in $I_{op}$, since the term is subtracted, the output line regulation coefficient is negative.

The foregoing regulation process does not hold for low levels. Directly after the switching transistors 58–61 are turned on, there is a high positive excursion of voltage across the resistors 63–66 which causes an immediate reset signal. This is due to the charging of capacitor 36 and can be overcome by the use of an extended set pulse driven by the monostable multivibrator 137 as set forth hereinabove. This extended set pulse forces the flip-flop output high regardless of the reset signal and takes care of this period of time. A shift between the monostable multivibrator and feedback modes is accomplished by diode 146 which limits the set pulse width.

The solid state switch which includes transistors 58–61 operates in a Class D mode with very little dissipation and therefore only a superficial heat sink is needed for the four transistors since dissipation of the switch is governed largely by the rapidity at which it is turned off. Directly after turnoff, the collector voltage may rise as high as 600 volts and any residual current causes much heating. Turnoff is speeded however, by capacitor 127 and transistors 83 and 84. When the dirver 28 turns off, the charge on capacitor 127 is fed into the base of transistor 84 which causes a 10 amp. current pulse to flow in transistor 83 to discharge the base-emitter capacitance of the switching transistors 58–61. This current pulse width is typically a 150 nanoseconds.

The fuses 52–55 represent failure mode protection against the shorting of the switching transistors. If an output transistor were to go into thermal runaway which was to result in a shorted junction, the transistor fuse would open allowing operation at reduced output. In addition, the comparator is protected from high voltage spikes by resistor 86.

While not meant to be limited thereto, the following is a list of components that have been utilized in a working embodiment of this invention: resistors in (ohms): 44, 45, 46 and 47 — 3,000; 63, 64, 65 and 66 — ½; 73, 74, 75 and 76 — 15; 85 — 10K; 86 — 2. 7K; 87 — 10K; 88 — 0 to 500; 89 — 330; 92 — 180; 93 — $R_t$ (selectable); 101 — 2.7K; 106 — 18K; 107 and 108 — 10K; 109 — 30K; 110 — 10K; 118 — 68o; 120 — 680; 123 — 33; 124 — ½; 126 — 120; 130 — 270; 131 — 270; 132 — ½; 143 — 2.7K; and 148 — 18K. Capacitors: 36 — 12,000 pf; 41 and 42 — .0047 (6KV); 90 — 0.1 µFd; 97 — 0.1µFd; 99 — 0.02; 103 — 0.1 µFd; 105 — 1200 pf; and 145 — 0.02; Transistors: 28 — GED 4572; 58, 59, 60 and 61 — Delco DTS 466; 83 — GED 4542; 84 — 2N2905A; 114 — 2N4275; 116 — 2N2905A; and 138 — MFE 3002. Diodes: 49 and 50 — Semtec 56F or Ge A115-M; 68, 69, 70 and 71 — 1N4148; 78, 79, 80 and 81 — GE A114-F; 91 — IN 4148; 135 — IN4148; and 146 — IN4148. Fuses: 52, 53, 54 and 55 — 18 amp. Integrated Chip Circuit: 98 — µA 7808. Amplifiers: 104 — ½µA 749; and 140 — ½µA 749. Comparator 20 — ½µA 749. NAND Gates: 100 — ⅓ CD 4023; 102 — ⅓ CD 4011 AE; 112 — ⅓ CD 4023; 113 — ¼ CD 4011 AE; and 141 — ⅓ CD 4023.

The signal generating device of this invention includes a tuned circuit tuned to a predetermined frequency wherein said tuned circuit includes an inductor, means connectable with a power source, switching means for connecting said means connectable with said power source with said tuned circuit for permitting current flow to said tuned circuit when said switching means is in a closed position and for preventing current flow to said tuned circuit when said switching means is in an open position, switching control means for causing said switching means to assume said closed position for a first period of time sufficient for current in the inductor of the tuned circuit to reach a predetermined level and for causing said switching means to assume said open position for a second period of time whereby the cyclic period of each combined first and second periods is substantially constant, and an output means connected with said tuned circuit whereby an RF decaying output signal regulated in power is produced during normal operation of said signal generating device.

The method of this invention for producing an RF regulated decaying output signal comprises providing a tuned circuit that oscillates at a predetermined frequency, establishing current flow to said tuned circuit, sensing the current flow through said tuned circuit, and repeatedly disrupting the current flow to said tuned circuit when said current reaches a predetermined level whereby the output from the tuned circuit is an RF decaying output signal regulated in power. The disrupting of the current flow occurs at a rate sufficient to establish an RF output signal suitable for surgical coagulation.

As can be seen from the foregoing, the signal generating device of this invention provides an improved device which is well suited for electrosurgical generators for producing surgical coagulation currents.

What is claimed is:

1. An electrosurgical method for coagulating tissue comprising the steps of
generating a D.C. voltage;
generating a pulse train having a predetermined pulse repetition frequency;
repetitively connecting said D.C. voltage across a tank circuit comprising at least a capacitor and a primary winding of a transformer, said capacitor and primary winding being in parallel connection and the resonant frequency of said tank circuit being substantially greater than said predetermined pulse repetition frequency, in response to each occurrence of a pulse of said pulse train to thereby store electrical energy in said tank circuit during each occurrence of said pulses;
repetitively disconnecting said D.C. voltage from said tank circuit in response to each termination of a pulse of said pulse train so that the said electrical energy stored in said tank circuit is coupled through a secondary winding of said transformer as a burst of pulses of decaying amplitude each time one of said pulses of said pulse train terminates, the capacitance of said capacitor and the inductance of said primary winding being such that crest factor of the output signal from said secondary winding is about 5 to 10;
applying said output signal to an electrosurgical instrument; and
coagulating said tissue by positioning said instrument adjacent said tissue.

2. The electrosurgical method of claim 1 including
generating a periodic signal having a frequency corresponding to said predetermined pulse repetition frequency;
sensing the current through said tank circuit each time it is connected to said D.C. voltage;
establishing a regulated, reference voltage;
comparing said reference voltage with a sensing voltage corresponding to the current sensed through said tank circuit;
said repetitive connecting step commencing with each cycle of said periodic signal;
said repetitive disconnecting step occurring each time said sensing voltage equals said reference voltage so that the output power from said tank circuit remains substantially constant in spite of variations in said D.C. voltage.

3. The electrosurgical method of claim 1 where said tank circuit includes resistive means in parallel with said capacitor and said primary winding, the value of said resistive means and the turns ratio of said primary and secondary windings being such that at least ten times more power is delivered from said tank circuit to a load impedance connected across said secondary winding than said resistive means for values of said load impedance between 200 and 2,000 ohms, said load impedance including the impedance of said tissue.

* * * * *